(12) United States Patent
Coelho et al.

(10) Patent No.: US 7,387,615 B2
(45) Date of Patent: Jun. 17, 2008

(54) SINGLE USE SYRINGE HAVING SAFETY SHIELD

(75) Inventors: Eduardo Pinto Coelho, Curitiba-Parana (BR); Delmar Francisco Goncalves Da Silva, Pinhais-Parana (BR); Amir A. Sharifi-Mehr, Bloomingdale, NJ (US); Gene Fleischer, New City, NY (US); Robert K. Cipoletti, Pompton Plains, NJ (US); Robert B. Odell, Flanklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 87 days.

(21) Appl. No.: 10/530,847

(22) PCT Filed: Oct. 2, 2003

(86) PCT No.: PCT/US03/31249

§ 371 (c)(1),
(2), (4) Date: Apr. 8, 2005

(87) PCT Pub. No.: WO2004/033008

PCT Pub. Date: Apr. 22, 2004

(65) Prior Publication Data

US 2006/0052748 A1    Mar. 9, 2006

(51) Int. Cl.
*A61M 5/00* (2006.01)
*A61M 5/32* (2006.01)

(52) U.S. Cl. .................. 604/110; 604/263; 604/192
(58) Field of Classification Search ............. 604/110, 604/228, 218, 220, 187, 215, 225, 212, 232, 604/229, 192, 263, 164.08
See application file for complete search history.

(56) References Cited

U.S. PATENT DOCUMENTS

| | | | | |
|---|---|---|---|---|
| 5,085,640 | A * | 2/1992 | Gibbs ...................... | 604/110 |
| 6,217,550 | B1 * | 4/2001 | Capes ...................... | 604/110 |
| 6,298,541 | B1 * | 10/2001 | Newby et al. ............. | 29/458 |
| 2002/0091361 | A1 * | 7/2002 | Rosoff et al. ............. | 604/212 |

* cited by examiner

*Primary Examiner*—Matthew F. Desanto
(74) *Attorney, Agent, or Firm*—Jeanne P. Lukasavage

(57) ABSTRACT

A single use syringe assembly includes a barrel having a chamber for retaining fluid, an open proximal end and a distal end including an elongate tip extending distally therefrom having a passageway therethrough in fluid communication with the chamber. A needle cannula having a lumen therethrough is connected to the elongate tip so that the lumen is in fluid communication with the passageway. An elongate needle shield having a longitudinal opening therein is hingedly connected to the barrel. A needle shield is capable of pivoting from an open position or a closed needle protecting position. The plunger including an elongate body portion and a stopper is slidably positioned in fluid-tight engagement with the inside surface of the barrel. Structure is provided for locking the plunger in the barrel by applying distally directed force to the plunger after fluid has been delivered from the chamber.

20 Claims, 20 Drawing Sheets

SINGLE USE SYRINGE HAVING SAFETY SHIELD

BACKGROUND OF THE INVENTION

The present invention relates generally to single use syringes having safety features and more specifically to a single use syringe having a plunger locking mechanism and safety shield.

In the United States and throughout the world, the multiple use of hypodermic syringe products that are intended for single use only, is instrumental in drug abuse and more particularly in the transfer of diseases. Intravenous drug users who routinely share and reuse syringes are a high-risk group with respect to the bloodborne pathogens including HIV and AIDS. Also the effects of multiple use are a major concern in under-developed countries where repeated use of syringe products may be responsible for the spread of many diseases. Reuse of single use hypodermic syringe assemblies is instrumental in the spread of drug abuse even in the absence of infection or disease.

Many attempts have been made to remedy this problem. Some of these attempts have required a specific act to destroy the syringe after use either by using a destructive device or providing a syringe assembly with frangible zones so that the syringe could be rendered inoperable by application of force. Other attempts have involved the inclusion of structure which would allow the destruction or defeating of the syringe function through a conscious act by the syringe user. Although many of these devices work quite well, they do require the specific intent of the user followed by the actual act to destroy or render the syringe inoperable.

Furthermore, in the medical arts, a syringe assembly typically includes a sharp pointed needle for administering fluids to patients either directly or into intravenous apparatus, and in various blood drawing applications either with syringes or with specialized holders for filling evacuated tubes. Since needles are widely used for medical procedures, many people can be exposed to needles in the routine course of their work.

Accidental needle sticks from used hypodermic needles can transmit disease. Accordingly, various types of needle shields such as hinged needle shields, have been designed to reduce the possibility of accidental sticks.

Various means have been provided for locking a hinged needle shield in the closed (needle protecting) position. Needles are available in a number of gauges and lengths so that they can be used for different purposes. Where a needle shield having a deflectable locking member is used to entrap a needle, it is important that the needle displace the locking member or members as it enters the needle shield cavity. It is also important that, since the needle is entrapped by the deflectable locking member or members, it cannot easily be displaced from the cavity. A relatively large diameter needle can more easily displace a deflectable locking member than a small diameter needle, both entering the needle shield cavity and exiting the cavity. As a needle shield should preferably be usable to protect needles of various sizes, the deflectable locking member or members should be designed such that it is sufficiently flexible to allow even a relatively small diameter needle to deflect it as it enters the needle shield cavity, but provides sufficient resistance to prevent the needle from being re-exposed through the opening of the cavity.

SUMMARY OF THE INVENTION

The present invention is directed to a single use syringe having multiple safety features. These safety features include a plunger locking mechanism, which when activated, locks the plunger in the barrel so that the syringe may not be reused. The plunger locking mechanism includes a locking ring on the plunger and a locking projection near the proximal portion of the barrel. Alternatively, the plunger locking mechanism may include a pair of locking rings or discs. The plunger locking mechanism further includes either a flexible portion on the plunger or a compressible stopper. When an additional axial load or force is applied to the proximal end of the plunger, the flexible portion of the plunger flexes allowing the locking ring to axial displace itself beyond the locking projection, thereby locking the plunger within the barrel. Alternatively, if a compressible stopper is used, when an additional axial force is applied to the proximal end of the plunger, the stopper compresses, allowing the locking ring to axially displace itself beyond the locking projection of the barrel, thereby locking the plunger in the barrel. The flexible plunger and the compressible stopper may be used together. Alternatively, a syringe assembly may include only one of the flexible plunger or the compressible stopper.

Another safety feature of the present invention is a breakable proximal portion of the plunger. After the plunger has been locked within the barrel, if an attempt is made to withdraw the plunger from the barrel, the proximal portion will detach or break off from the plunger to ensure that the syringe is not reused.

Yet another safety feature of the present invention is a hinged shield for shielding the needle cannula after an injection The present invention is advantageous because each of the safety features may be activated using a single hand. Another advantage of the present invention, is that conventional procedures for performing an injection may be utilized.

A single use syringe of the present invention comprises a barrel including a cylindrical side wall having an inside surface defining a chamber for retaining fluid. The barrel includes an open proximal end and a distal end having a distal wall with an elongate tip extending distally therefrom having a passageway therethrough in fluid communication with the chamber. A needle cannula having a proximal end, a distal end and a lumen therethrough is connected to the elongate tip so that the lumen is in fluid communication with the passageway of the tip. The connection of the needle cannula to the tip can be either directly or indirectly through a hub attached to the needle cannula. An elongate needle shield is hingedly connected to the barrel. The needle shield includes two sidewalls defining a longitudinal opening and a back wall between the sidewalls defining a recess having an interior surface. The needle shield is capable of pivoting from an open position wherein the needle cannula is exposed, to a closed needle protecting position wherein the distal end of the needle cannula is within the longitudinal opening of the shield. A plunger including an elongate body portion having a proximal portion and a distal portion and a stopper is slidably positioned in fluid-tight engagement with the inside surface of the barrel for drawing fluid into and driving fluid out of the chamber by movement of the stopper relative to the barrel. The elongate body portion extends outwardly from the open proximal end of the barrel. The syringe assembly further includes means for locking the plunger in the barrel by applying an additional distally directed force to the plunger after fluid has been delivered from the chamber.

The syringe assembly may also include plunger weakening structure for allowing the plunger to break upon application of excessive force intended to move the plunger proximally after the plunger has been locked in the barrel. This structure may take the form of a reduced cross-sectional thickness in the proximal portion of the elongate body portion of the plunger.

Means for locking the plunger to the barrel may include a contractible portion on the plunger, a discontinuity on the plunger and a discontinuity on the barrel. The plunger discontinuity is capable of engaging the barrel discontinuity when an additional distally directed force which is applied to the plunger shortens the contractible portion so that the plunger discontinuity moves distally to engage the barrel discontinuity to lock the plunger in the barrel. The barrel discontinuity may be a recess or a projection and is preferably an inwardly directed projection in the shape of an annular ring. Likewise, discontinuity on the plunger may be a recess or a projection. The discontinuity is preferably an outwardly directed projection in the shape of an annular ring.

The contractible portion of the plunger may include one or more flexible elements traversing a gap in the elongate body portion. The one or more elements are capable of withstanding the forces of fluid delivery and deflectable upon application of an additional force to the plunger. The contractible portion may also include a cavity formed by the distal end of the plunger and the interior surface of the stopper wherein the plunger moves into the cavity upon application of the additional force to effectively shorten the length of the plunger.

The syringe assembly may further include structure for locking the needle shield in the closed needle protecting position when the needle shield is pivoted into the closed position. The needle shield locking structure may include an arm projecting from the interior surface of the needle shield. The arm includes a free end positioned so that when the needle shield is pivoted to the closed position, the needle cannula moves past the free end and is trapped in the needle shield by the arm. The needle shield locking structure may also include locking members on the proximal end of the needle shield capable of engaging a cooperating ledge at the distal end of the barrel when the needle shield is pivoted to the closed position.

The syringe assembly may further include a needle assembly comprising the needle cannula and a hub having an open proximal end containing a cavity and a distal end attached to the proximal end of the cannula so that the lumen is in fluid communication with the cavity of the hub. The needle assembly is removably attached to the tip of the barrel by engagement of the tip in the cavity of the hub so that a lumen is in fluid communication with the chamber.

DETAILED DESCRIPTION

Figure 1:
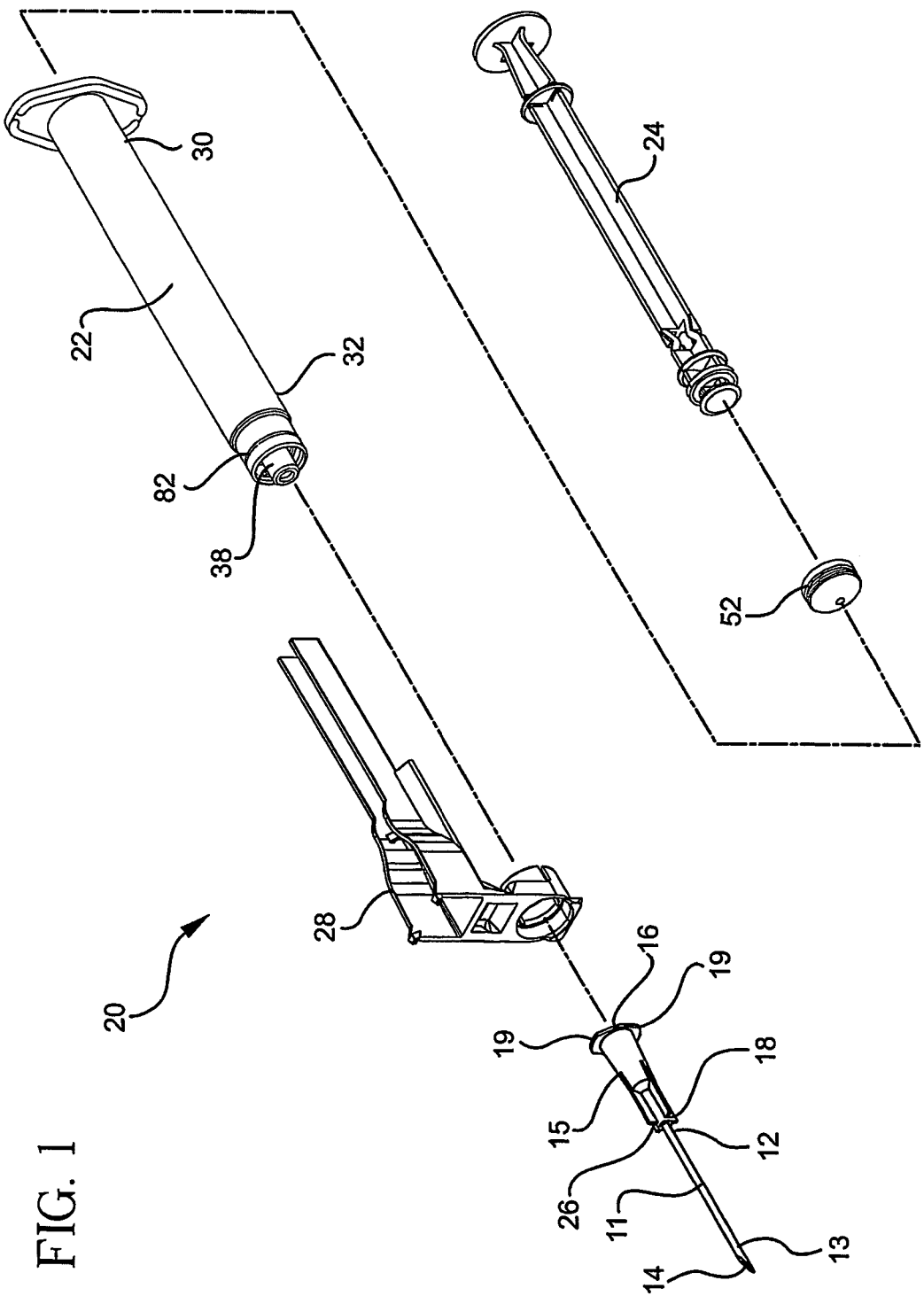
FIG. 1 is an exploded perspective view of the syringe assembly according to the present invention.
Figure 1A:
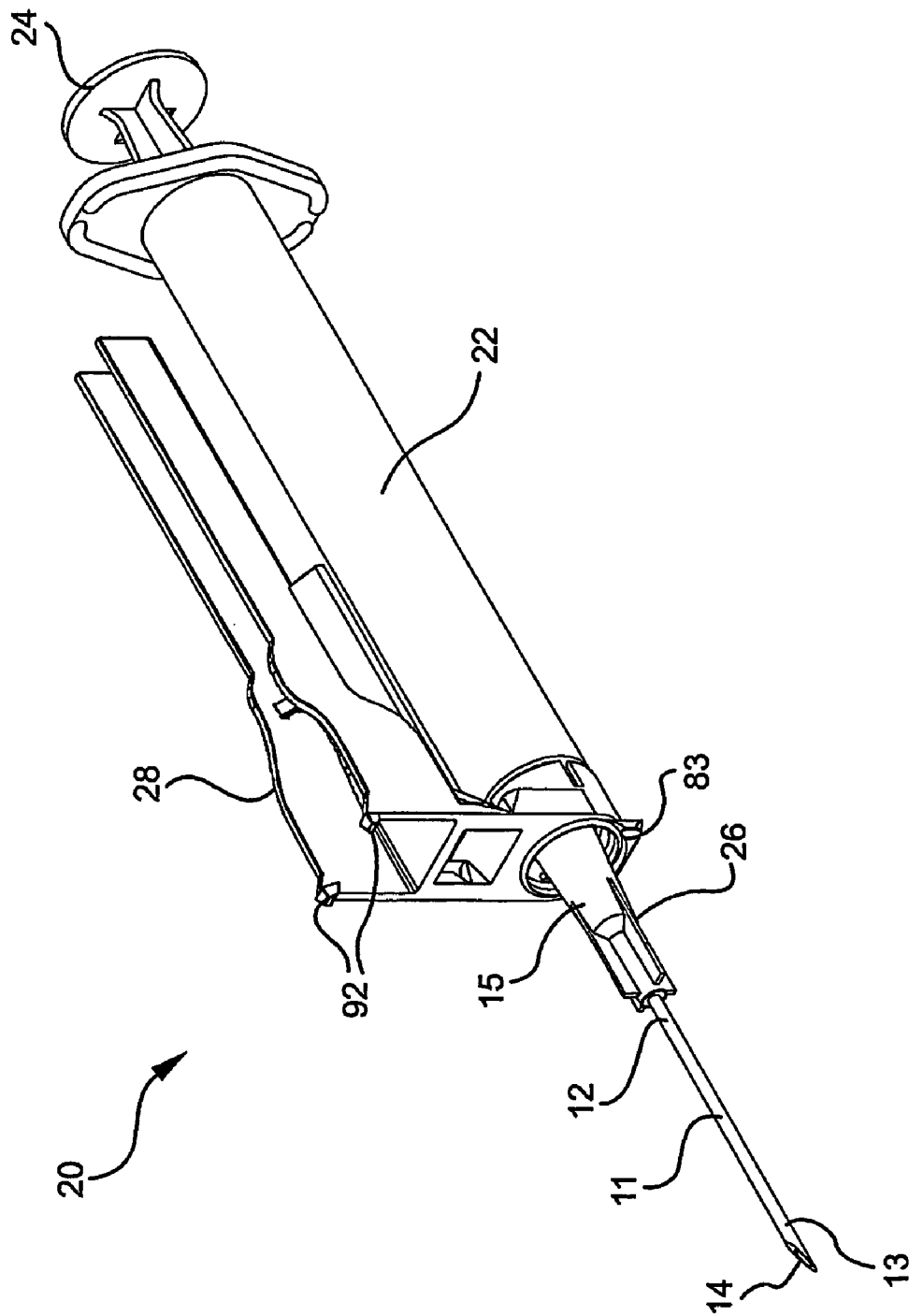
FIG. 1A is a perspective view of the syringe assembly according to the present invention.
Figure 2:
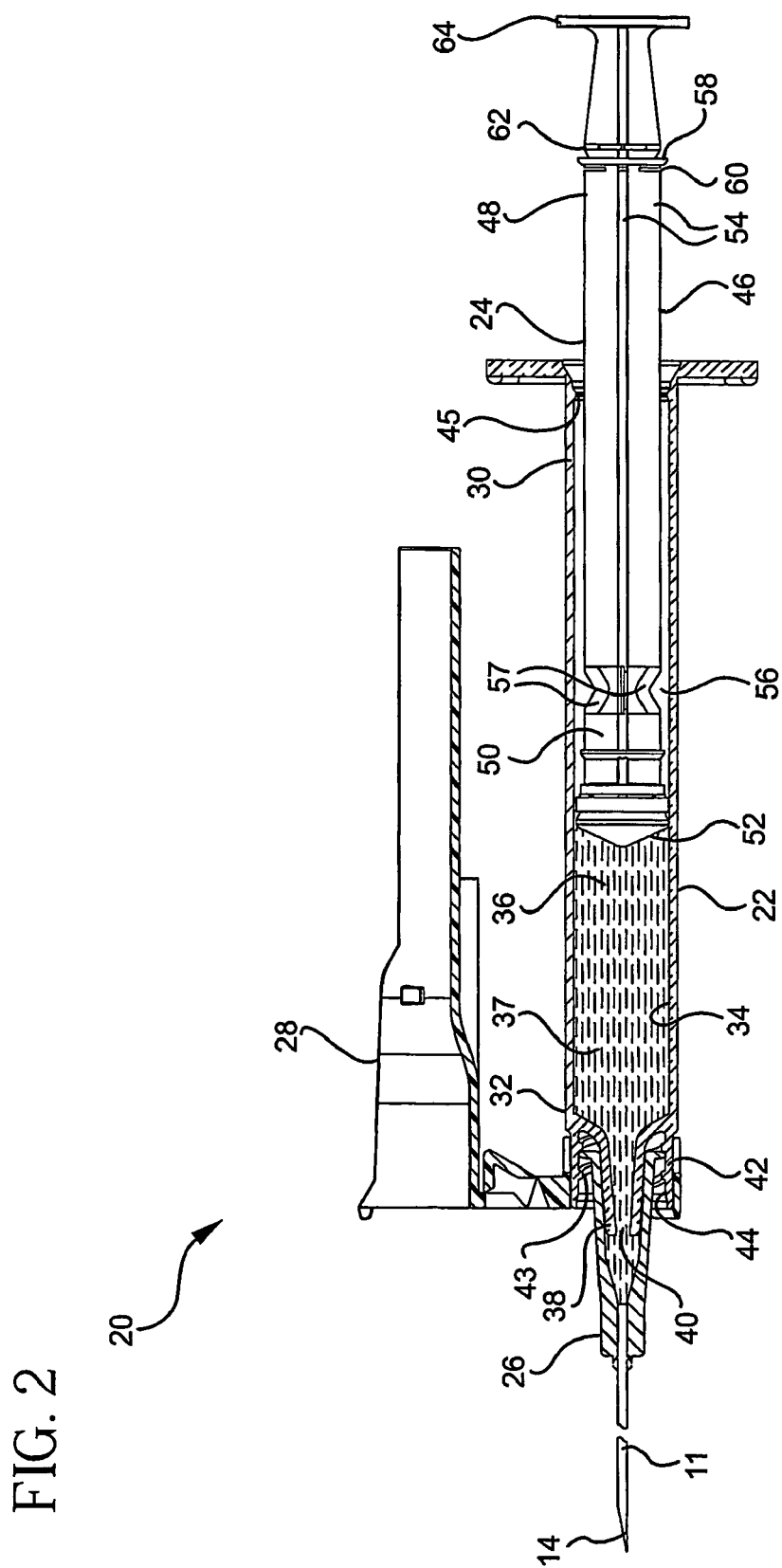
FIG. 2 is a cross-sectional side elevation view of the syringe assembly of the present invention, with the plunger in position to perform an injection.

Referring to FIGS. 1-5A, a syringe assembly 20 according to the present invention, generally comprises a barrel 22, a plunger 24, a needle assembly 26 and a safety shield assembly 28.

Barrel 22 includes a proximal end 30, a distal end 32, an inside surface 34, a fluid chamber 36 and an elongate tip 38 extending from distal end 32 having a passageway 40 therethrough in fluid communication with chamber 36. The barrel further includes a collar 42 around elongate tip 38 having a thread 43 on an inside surface 44 of the collar. This configuration is often referred to as a locking luer collar. The present invention contemplates the utilization of any type of syringe barrel and needle or needle assembly assembly, and not just a syringe having a locking luer collar. Thus, embodiments of the present invention may include an integral needle and syringe barrel, a luer slip tip with or without a collar, or any other needle/syringe configuration. A discontinuity such as locking projection 45 extends inwardly from the inside surface 34 of the barrel at its proximal end 30. As shown, the locking projection 45 is an annular ring. It is within the purview of the present invention for the discontinuity to have various shapes and configurations, including locking barbs, as long as the discontinuity locks the plunger in the barrel upon activation, as will be discussed below.

Syringe assembly 20 of the present embodiment preferably includes a needle assembly 26 having a cannula 11 having a proximal end 12, a distal end 13 and a lumen 14 therethrough. The needle assembly further includes a hub 15 having an open proximal end 16 having a cavity 17 therein, and a distal end 18 joined to proximal end 12 of cannula 13 so that lumen 14 is in fluid communication with cavity 17. The hub includes outwardly extending projections 19 and is placed on the distal end of barrel 22 by aligning the distal end of the barrel with the cavity in the hub so that the outward projections 19 of the hub engage thread 43 in the collar. Needle assembly 26 is then rotated or screwed into the locking luer collar 42 so that the needle assembly is held tightly on the distal end 32 of the syringe barrel 22 through interaction of the locking luer collar thread 43 and the projections 19 on the needle hub and a frictional interference fit between elongate tip 38 on the barrel and cavity 17 in the hub. Thus, the lumen 14 is in fluid communication with fluid chamber 36. It is within the purview of the present invention to include a needle assembly having one-piece construction wherein the cannula and the hub are formed of one piece and a cannula attached directly to the barrel without the use of a hub.

Plunger 24 includes an elongate body portion 46 having a proximal portion 48, a distal portion 50 and a stopper 52 disposed on the end of distal portion 50. Elongate body 46 includes a plurality of outwardly projecting axial ribs 54. Preferably, the plunger includes four ribs, but may include fewer or more than four ribs. According to the present invention, the plunger defines contractible portion 56. The term contractible portion as used herein shall include structure which is flexible, collapsible, breakable and/or deformable or the like. Preferably contractible portion 56 is located along the distal portion of the plunger, but may be located anywhere along the plunger. In this embodiment, the contractible portion comprises flexing elements 57 disposed on each of the ribs. Each of the flexing elements in this embodiment, comprises a weakened portion of the rib that flexes or bends inwardly. Contractible portion 56 of the plunger is capable of withstanding the axial load of a typical injection. Application of an axial force greater than that required for a typical injection will result in the contractible portion of the plunger flexing deforming, breaking and/or collapsing, as will be discussed in greater detail below. Thus, the flexing elements 57 of this embodiment are strong enough to withstand the axial load of injection during normal use of a syringe.

Plunger 24 further includes a discontinuity such as annular locking ring 58 that is preferably located on proximal portion 48. In this embodiment, the locking ring is preferably chamfered such that its diameter decreases in the distal direction. On the distal side of the locking ring 58, each rib preferably includes a slot 60. On the proximal side of the locking ring, each rib is configured to define a break point 62. At its proximal end, the plunger includes a thumb press 64.

Stopper 52 includes an inside surface 66 and an outside surface 68. The stopper 52 fits over distal portion 50 of plunger 24 at an annular distal end 70 of the plunger. Inside surface 66 of the stopper includes an annular groove 72 for receiving the annular distal end 70 of the plunger. Thus, the stopper fits onto the plunger in a snap fit arrangement. Friction may also play a role in fitting the stopper onto the distal end of the plunger. The stopper further defines a cavity 74. The outside surface 68 of the stopper includes at least one seal rib 76 for sealing engagement with inside surface 34 of barrel 22. The plunger further includes a distal shoulder 78 abutting the proximal end of stopper 52.

Figure 6:
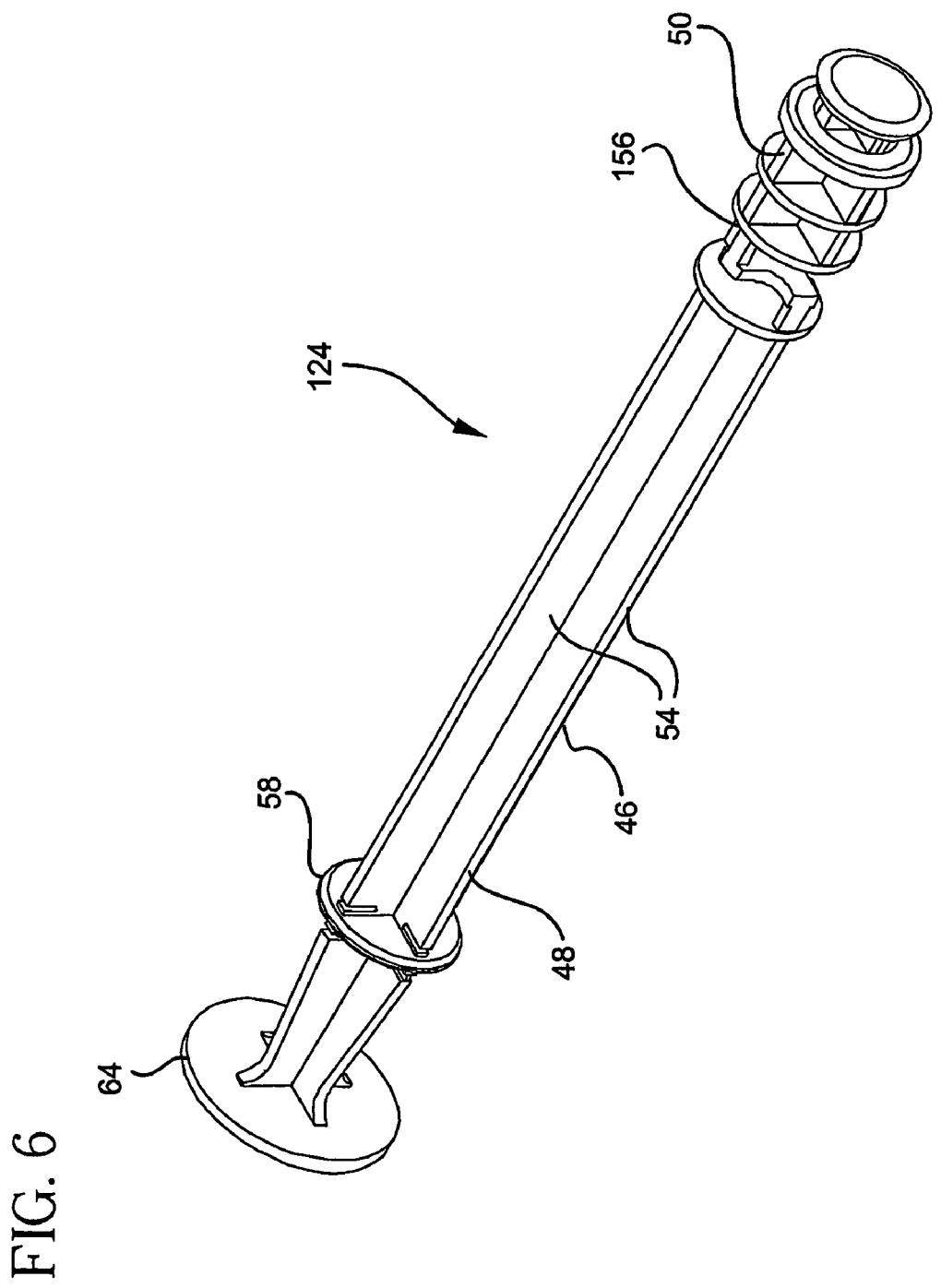
FIG. 6 is a perspective view of a plunger according to another embodiment of the present invention.
Figure 6B:
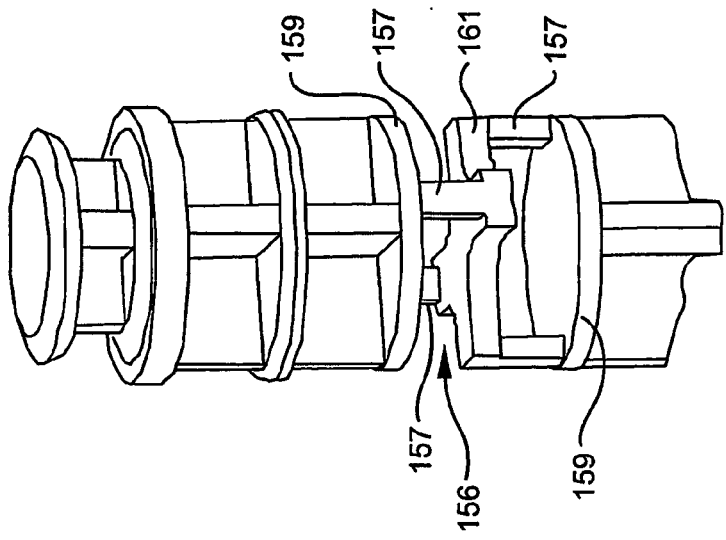
FIG. 6B is an enlarged perspective view of the distal portion of the plunger of FIG. 6.
Figure 6A:
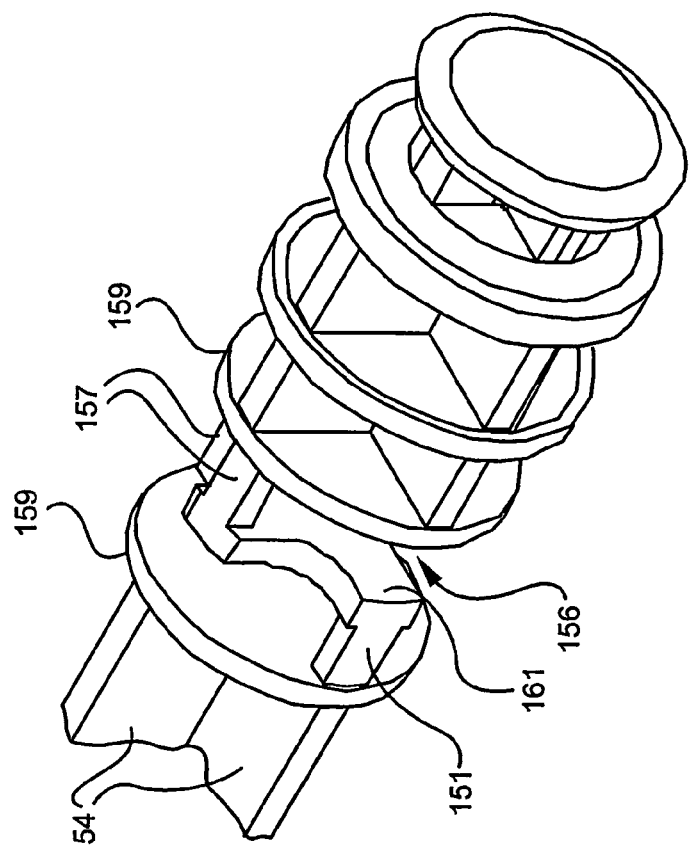
FIG. 6A is an enlarged perspective view of the contractible portion of the plunger of FIG. 6.
Figure 6C:
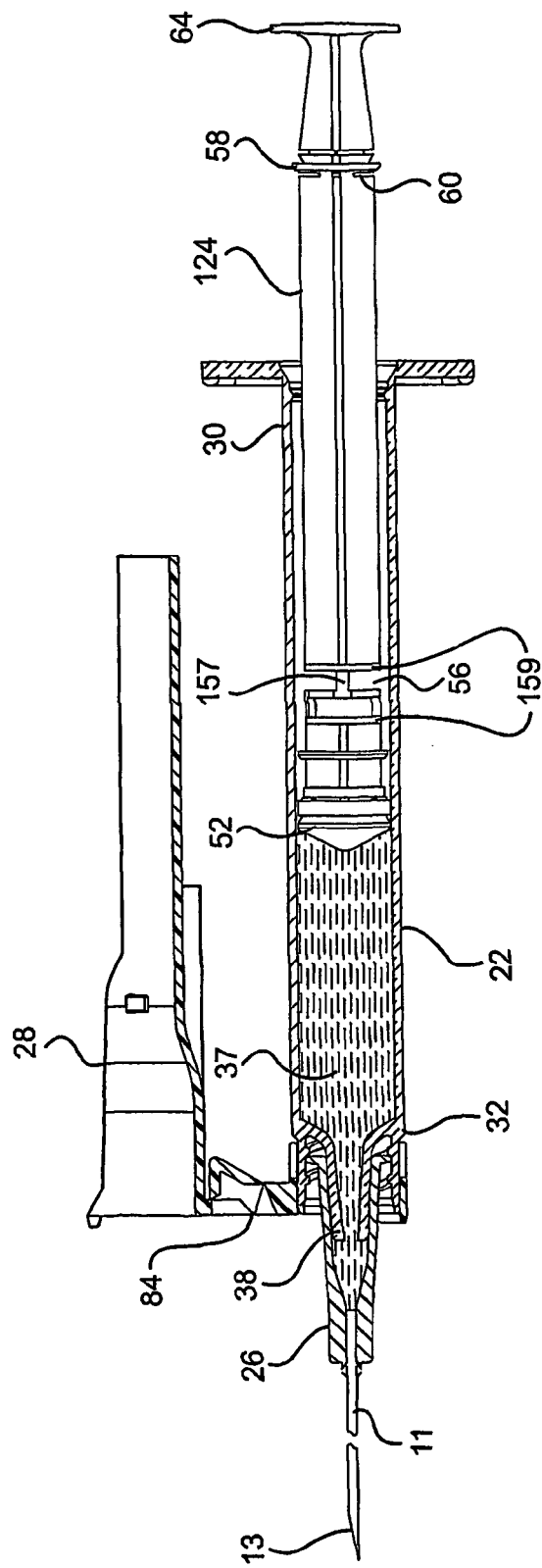
FIG. 6C is a partial cross-sectional side elevation view of the syringe assembly of FIG. 6 with the plunger in position to perform an injection.
Figure 7:
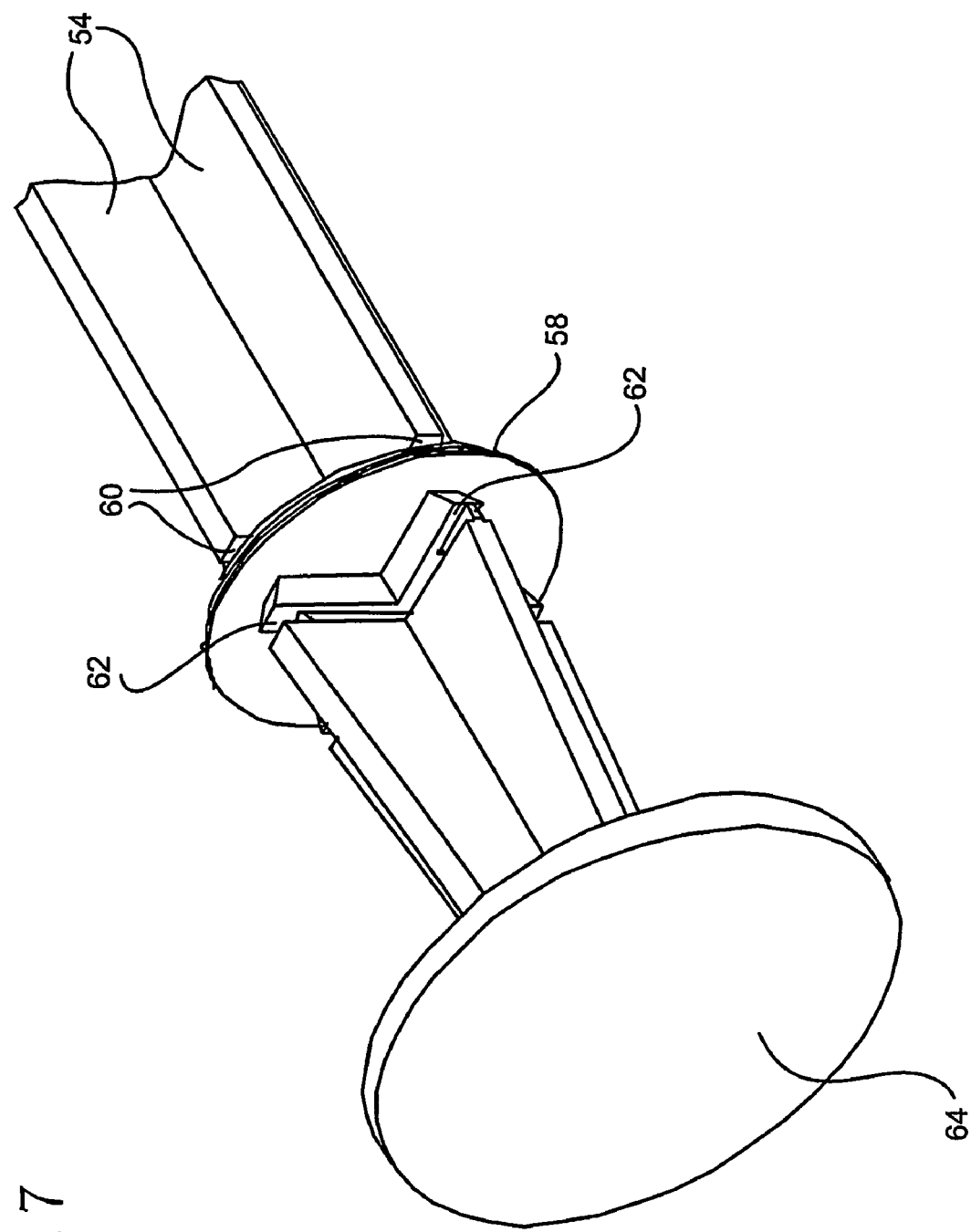
FIG. 7 is a partial perspective view of the proximal portion of the plunger according to the present invention.

FIG. 6, 6A and 6B show an alternate embodiment of the invention where like parts are similarly numbered. A plunger 124 includes a contractible portion 156 comprising a pair of platforms 159, each preferably having two pairs of flexing columns 157 extending therefrom and attaching to a flexing platform 161. The pairs of columns 157 are offset from each other preferably by 180 degrees. Flexing portion 156 is capable of withstanding the axial load of a typical injection. Application of an axial force greater than that required for a typical injection will result in the contractible portion 156 of the plunger flexing, as will be discussed in greater detail below.

Figure 8:
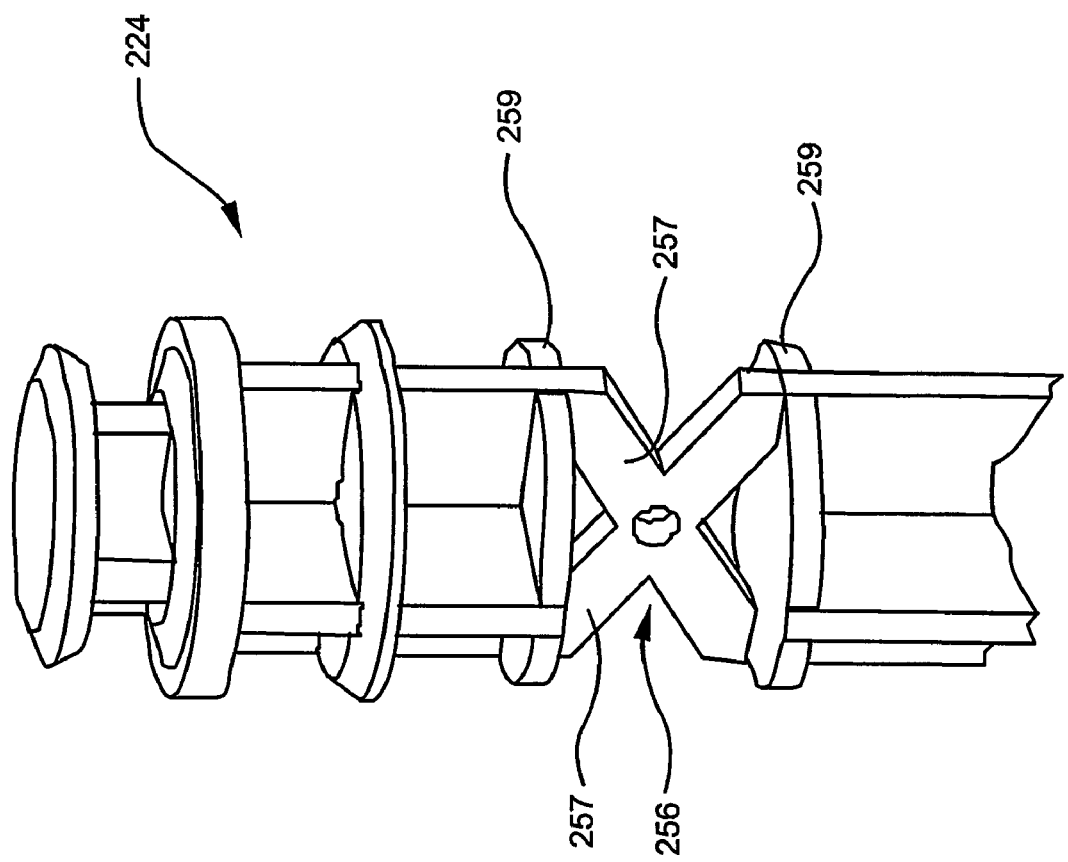
FIG. 8 is an enlarged perspective view of the distal end of a plunger according to still another embodiment of the invention.
Figure 9:
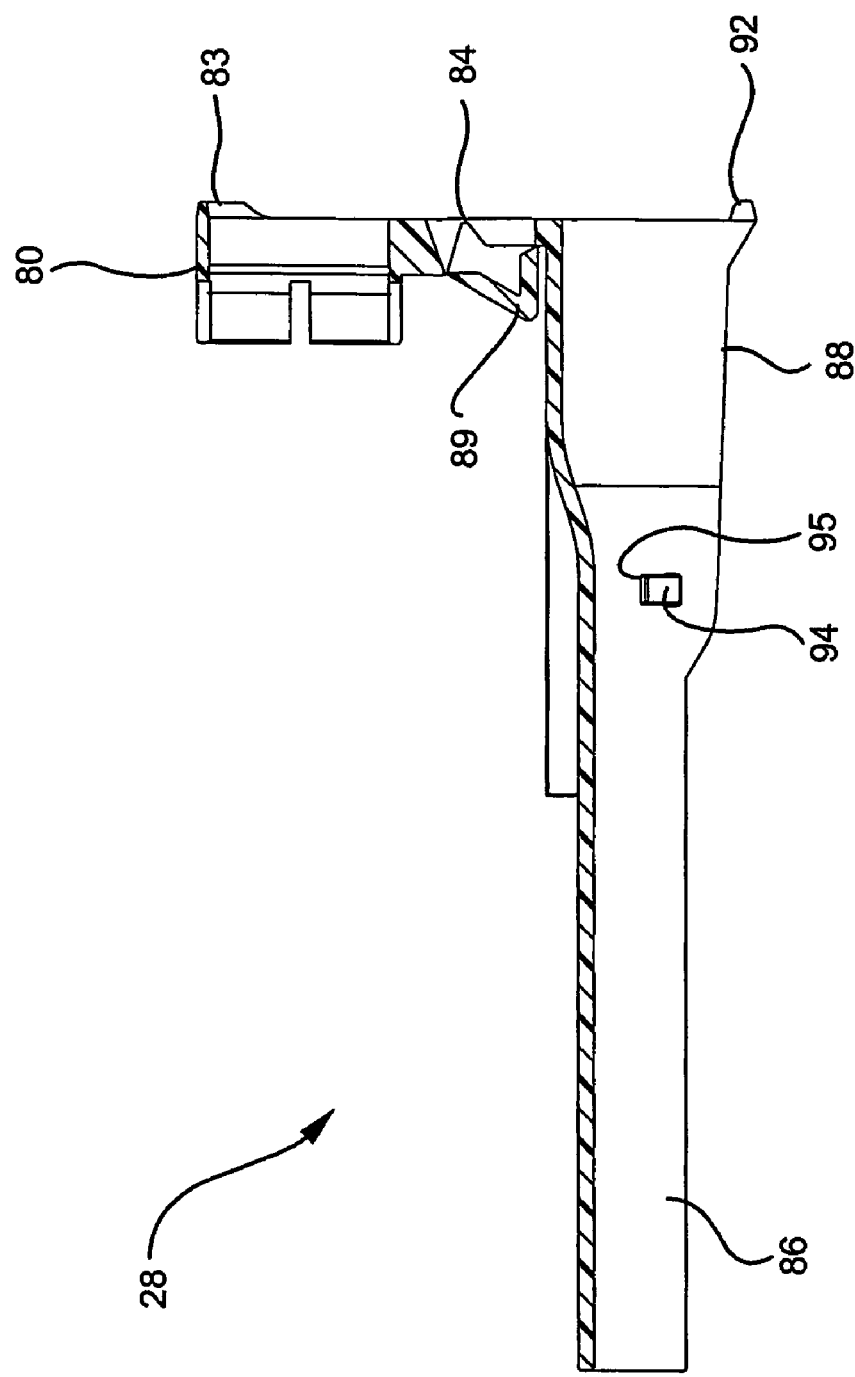
FIG. 9 is a cross sectional side elevation view of the safety shield of FIG. 1.
Figure 9A:
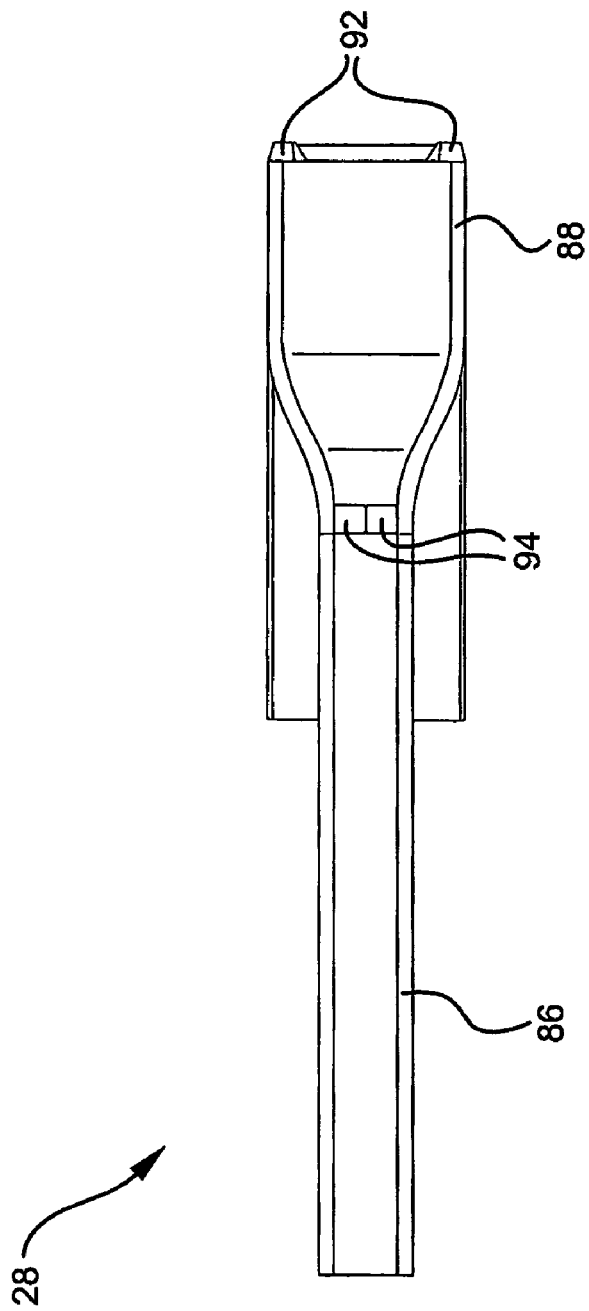
FIG. 9A is a bottom plan view of the safety shield of FIG. 1
Figure 9B:
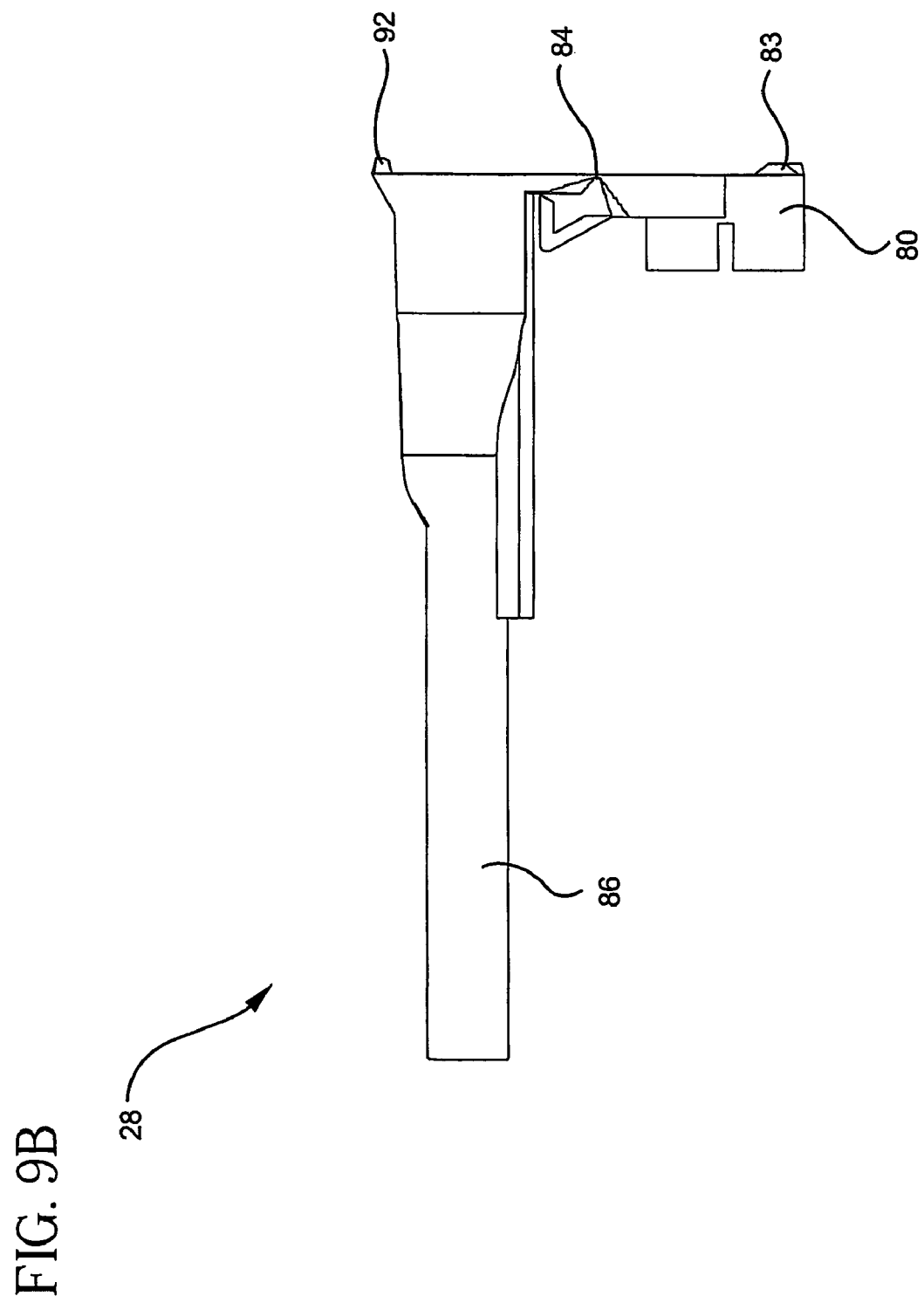
FIG. 9B is a side elevation view of the safety shield of FIG. 1.
Figure 10:
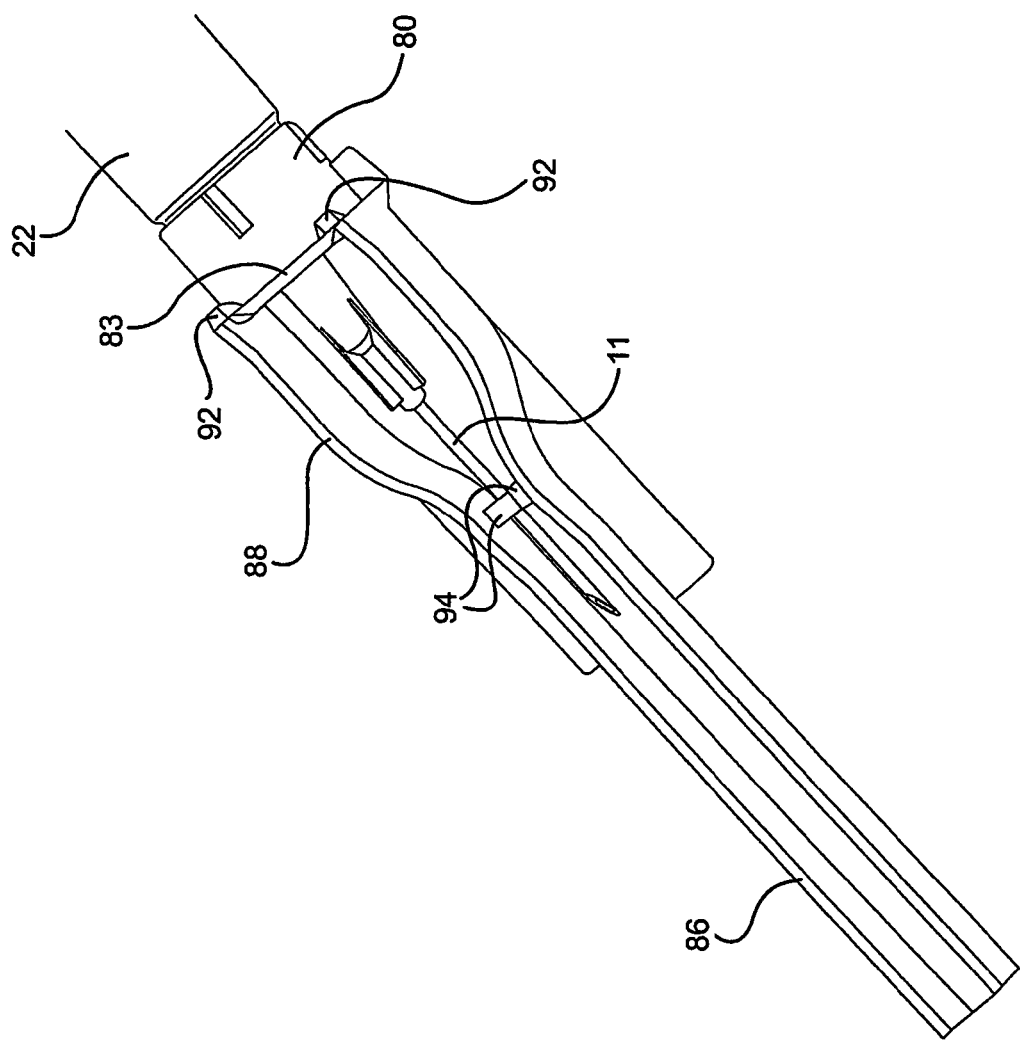
FIG. 10 is a bottom perspective view of the safety shield of FIG. 1 in its closed position.

FIG. 8 shows yet another embodiment of a plunger 224 according to the present invention where like parts are similarly numbered. Plunger 224 includes a contractible portion 256 comprising comprises two crossing flex members 257 connecting a pair of platforms 259. Contractible portion 256 is capable of withstanding the axial load of a typical injection. Application of an axial force greater than that required for a typical injection will result in contractible portion 256 of the plunger flexing collapsing, breaking and/or deforming, as will be discussed in greater detail below. It is within the purview of the present invention to include plunger rods having different geometries, shapes and materials for the contractible portion.

FIGS. 9, 9A, 9B and 10 show the safety shield 28. The safety shield comprises a hub 80 for engagement with collar 42 of barrel 22. Hub 80 includes mating geometry on its inside surface that cooperates with an annular ring 82 on collar 42 of the barrel. The mating geometry may be, for example an annular ring or a pair of projections extending from the inside surface of hub 80. Thus, the shield attaches onto the collar via the hub in a snap fit arrangement. It is within the purview of this invention to provide for mating of the hub and collar other than a snap fit, such as an interference fit, threads, adhesive, welding, deformation and the like.

The hub further includes edge 83 extending from its proximal end. Shield 28 further comprises a hinge that preferably includes a living hinge such as hinge 84. Hinge 84 connects the hub 80 to a shield member 86. Shield member 86 includes proximal portion 88 and distal portion 90. The proximal portion 88 includes locking members 92. Locking members 92 cooperate and latch onto ledge 83 when the safety shield is activated by moving it to the needle protecting position. Proximal portion 88 is wide enough to receive needle hub 15, when the safety shield is activated.

Distal portion 90 of the shield member receives and retains the needle cannula 11 when the safety shield is activated, that is, pivoted to its needle protecting position. Needle cannula 11 is secured within the distal portion 90 of the shield member 86 by retaining members or arms 94 having free ends 95, preferably located on the interior surface of shield member 86. Retaining members 94 allow for the needle cannula to pass therebetween while the shield member is rotated into activation, and are angled so that the needle is locked behind the retaining members once shield member 86 is fully activated and locked by locking members 92.

According to the present invention, the syringe assembly includes several features that can be used separately or in combination to ensure that syringe is used only a single time. Referring now to all of the figures, especially FIGS. 3 and 11, the operation of the syringe assembly is described. In operation, the syringe can be filled from a vial, ampoule or other suitable container using know safe procedures. The syringe is filled by inserting the needle cannula into a vial and withdrawing the plunger 24. This will cause the liquid to be drawn through the lumen of the needle cannula and into fluid chamber 36. An important advantage of the present invention is that the plunger can be moved back and forth along the barrel as many times as necessary to properly fill the fluid chamber. For example, the syringe barrel may be filled with sterile water and the sterile water can be injected into a vial contain lyophilized medication which is then drawn back into the syringe barrel. Contractible portion 56 of the plunger is strong enough to withstand the axial forces necessary for filling the syringe. Many single use syringes in the prior art only allow one proximal motion of the plunger with respect to the barrel. With these prior art single use syringes, once the plunger is moved in a distal direction with respect to the barrel, it can no longer be withdrawn. Therefore, mixing sterile water and a lyophilized medication as described above is not possible.

Fluid 37 in fluid chamber 36 can now be injected into a patient or delivered in another suitable manner such as through the pierceable septum of a catheter connector. This occurs by applying an axial force to the thumb press 64 to cause plunger 24 to advance within barrel 22, thereby expelling the fluid through the lumen of needle cannula 11. The position of the plunger at the end of the injection is shown in FIG. 3.

Figure 3:
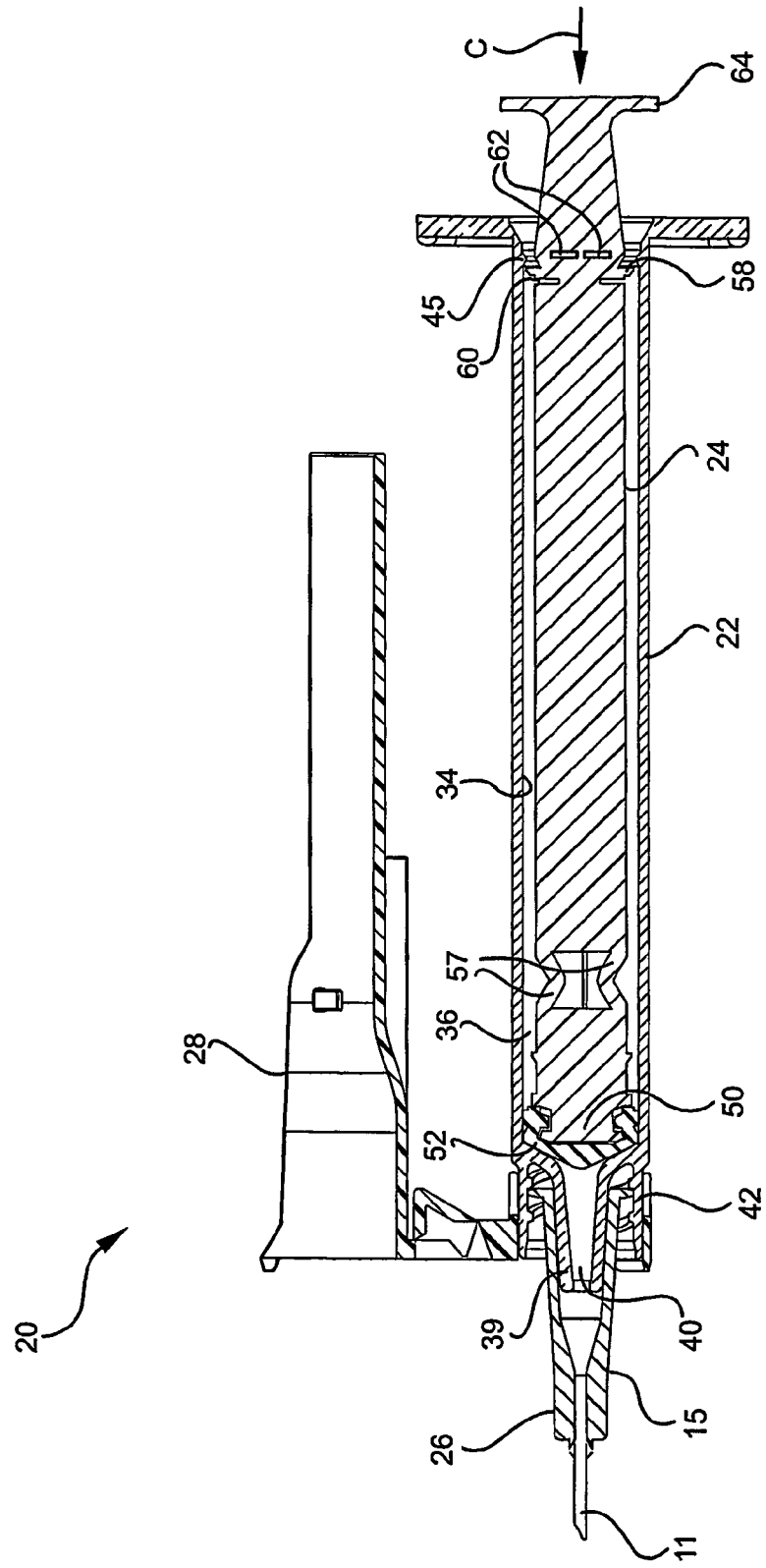
FIG. 3 is a cross-sectional side elevation view of the syringe assembly of FIG. 2, with the plunger in position after an injection has been performed.
Figure 3A:
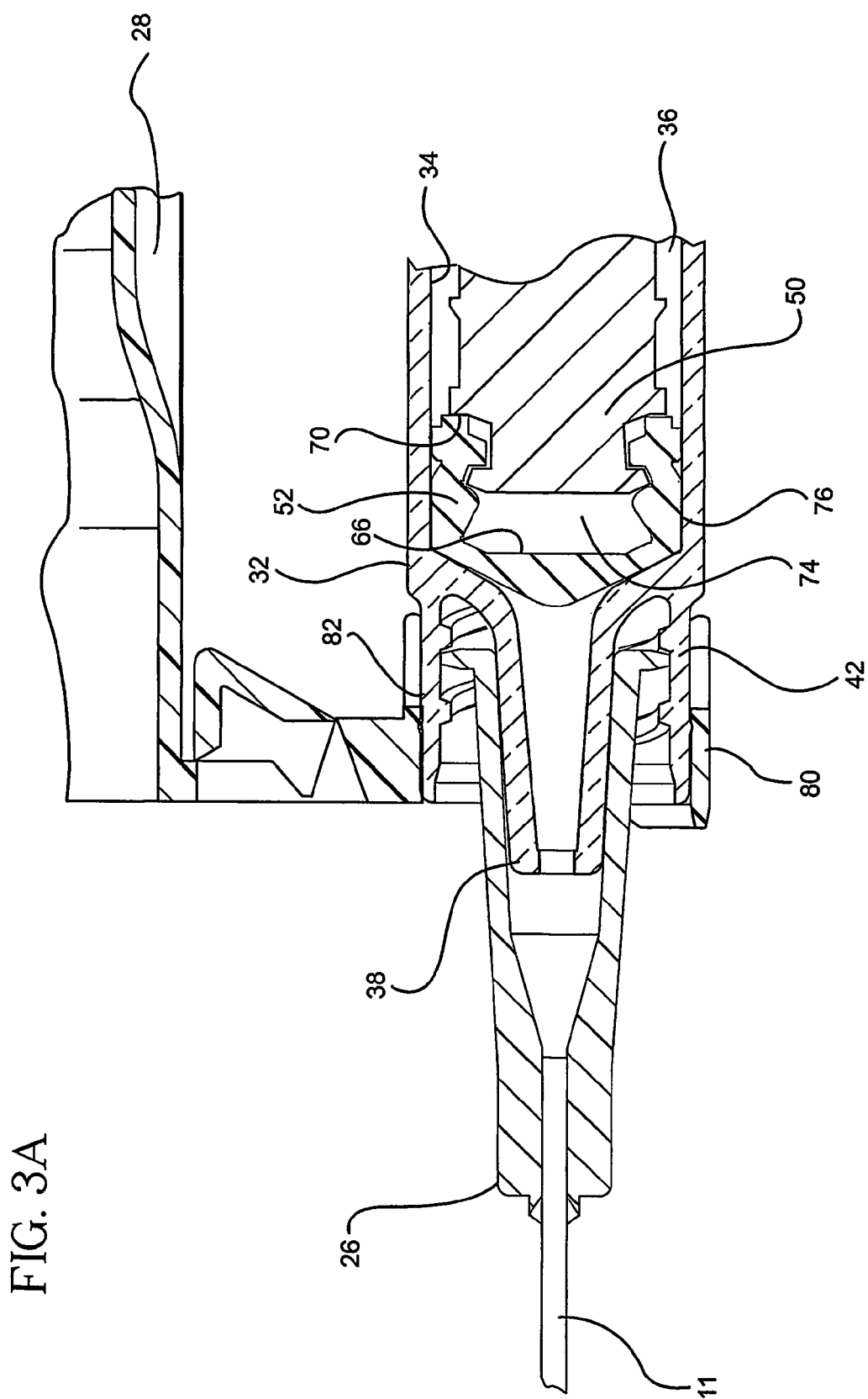
FIG. 3A is an enlarged cross-sectional side elevation view of the distal end of the syringe assembly of FIG. 3.
Figure 4:
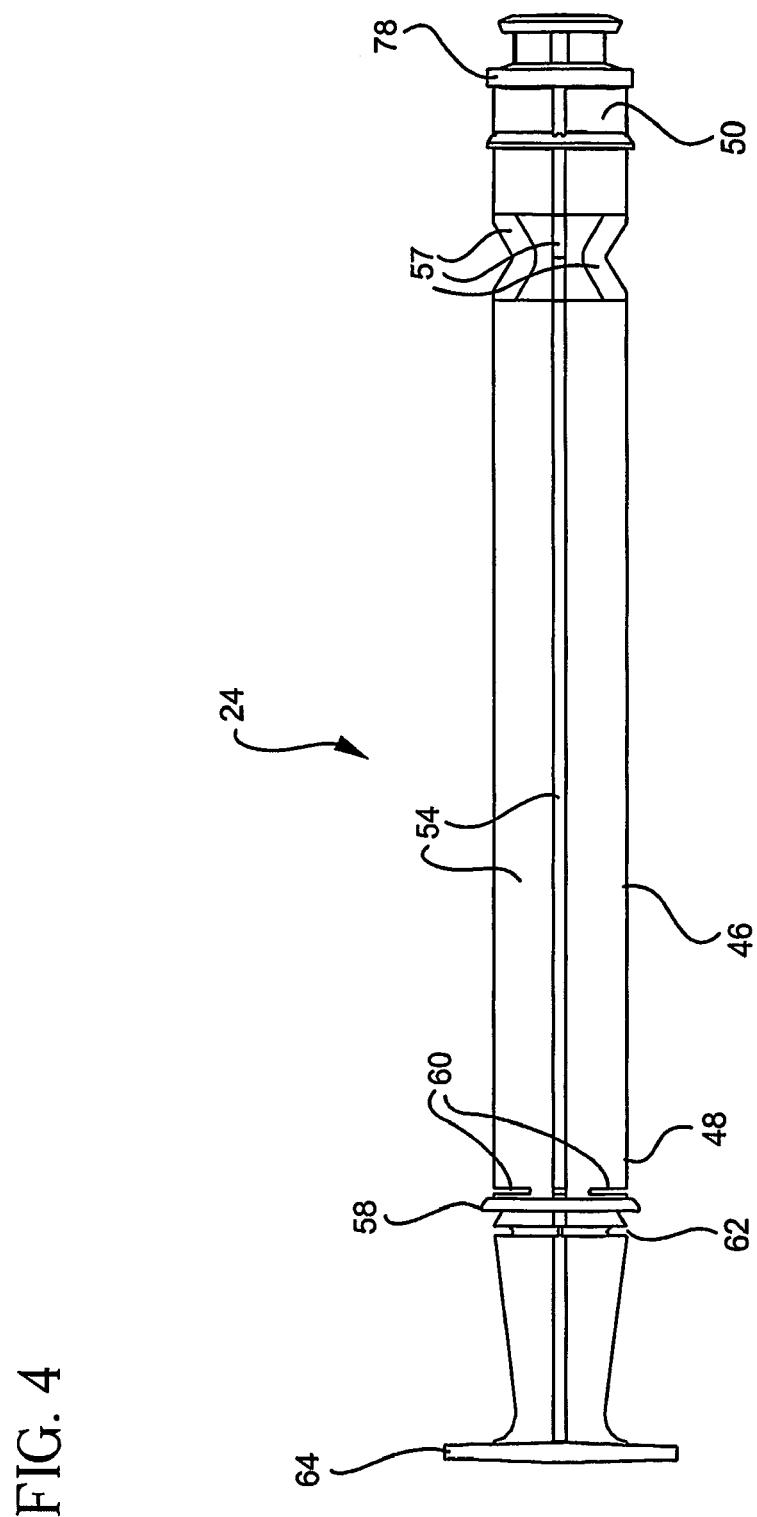
FIG. 4 is a side elevation view of the plunger of FIG. 2.
Figure 5:
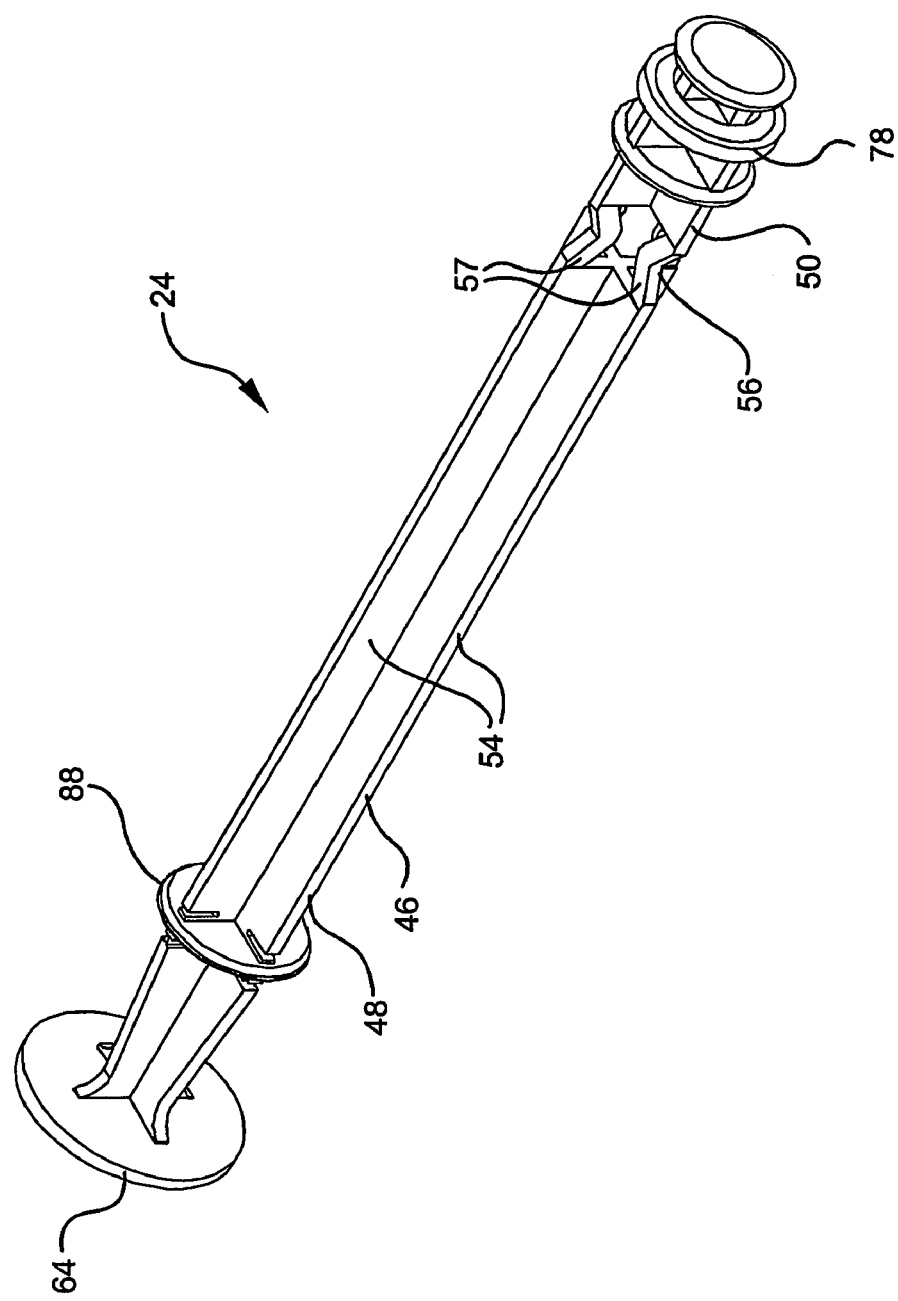
FIG. 5 is a perspective view of the plunger of FIG. 2.
Figure 5A:
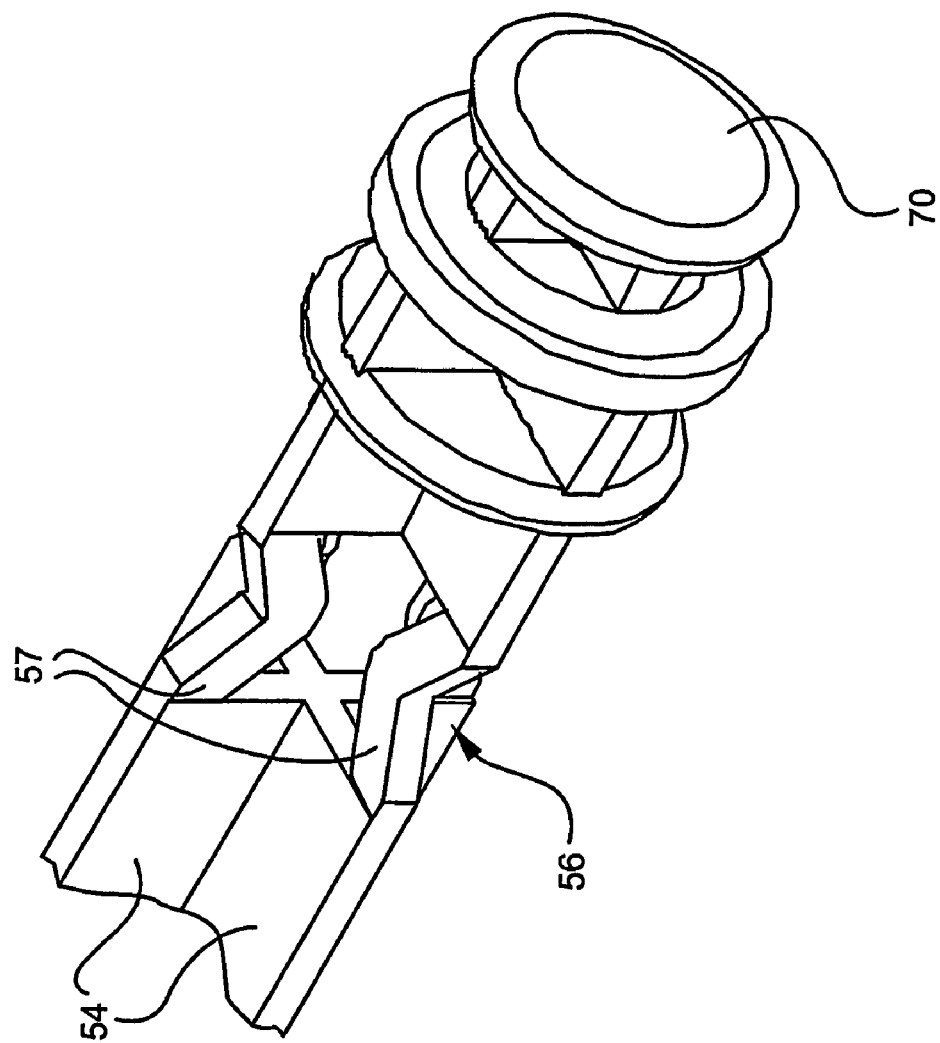
FIG. 5A is an enlarged perspective view of the contractible portion of the plunger of FIG. 5.
Figure 11:
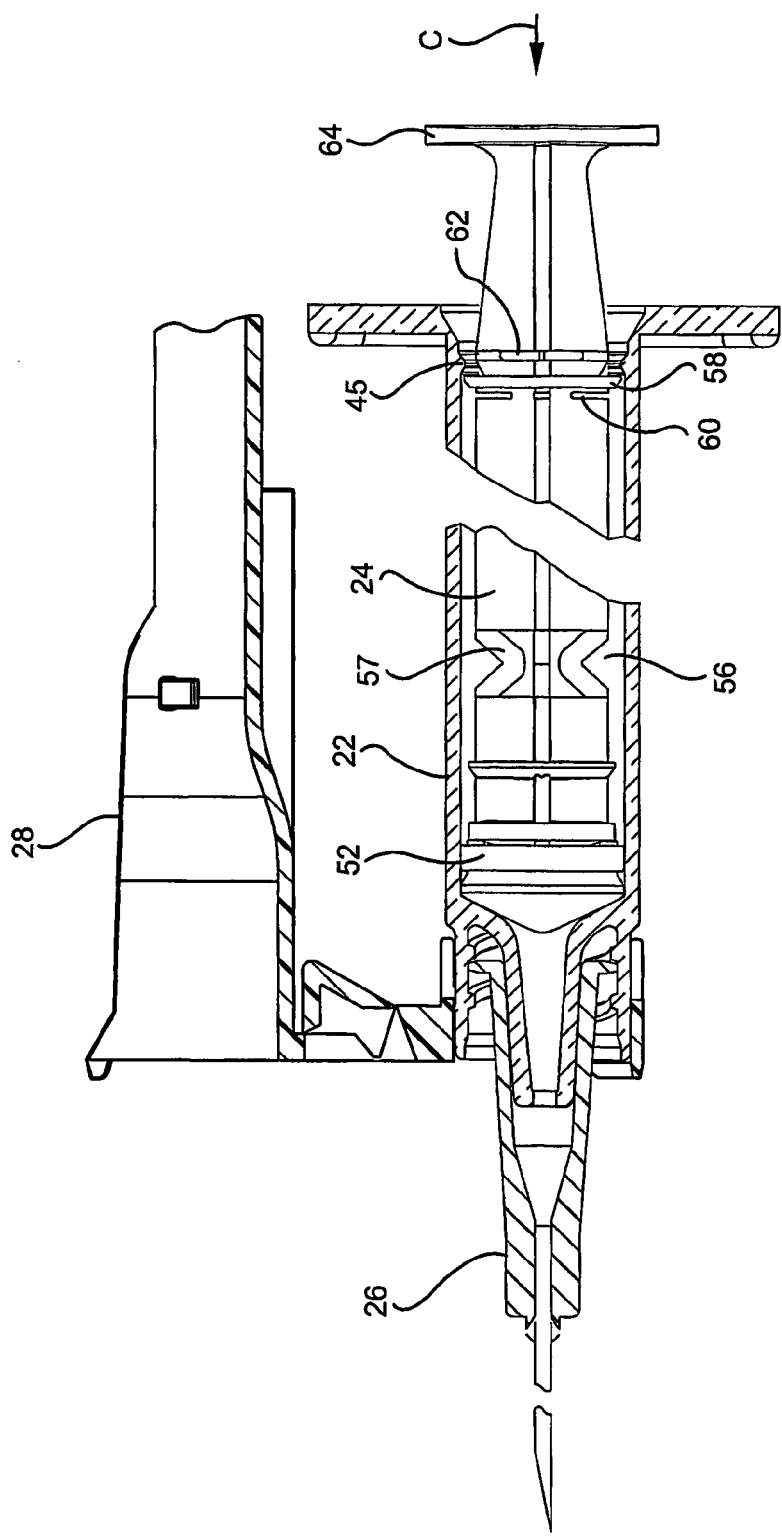
FIG. 11 is a partial cross sectional view of the syringe assembly of FIG. 2, after the plunger locking mechanism has been activated.

Upon completion of the injection, an additional axial force indicated as C in FIG. 3 is applied to the proximal portion of the plunger, preferably on thumb press 64. FIG. 11 shows the plunger in the locked position after the additional axial force C has been applied to the plunger. The additional axial force causes the flexing portions 57 to flex inwardly. As the flexing portions flex, the additional axial force further causes locking ring 58 on the plunger to advance distally in the barrel past locking projection 45, in the barrel, as shown in FIG. 11. Thus, the plunger is locked in the barrel and the syringe is disabled and unusable.

In addition to or as an alternative to the action of the flexing portions, the additional axial force can cause the stopper 52 to compress to allow for distal axial movement of the locking ring 58 into the locked position. The compression of the stopper 52 allows the distal end 70 of the plunger to axially advance within the chamber 74 of the stopper 52. This, in turn, allows for axial travel of locking ring 58 in barrel 22 to a position beyond locking projection 45. The plunger 24, therefore, is locked in the barrel via the locking ring being advance beyond locking projection 45 of the barrel. Thus, the syringe is disabled and rendered unusable.

An alternate embodiment of the invention may include a support pin on the distal end 70 of the plunger. The support pin would support the stopper during an injection. In addition, at the end of the injection, the support pin may pierce or puncture the stopper, if the compression of the stopper does not provide enough axial travel for the locking ring to lock.

The present invention contemplates the use of contractible portion 56 of the plunger and the compressible stopper 52 either in combination or separately to achieve the axial travel required to lock the locking ring 58 in position beyond the locking projection 45. Thus, a plunger having a contractible portion 56 according to the present invention may be used in a two-piece syringe assembly, where there is no stopper and the plunger and the stopper are integrally formed, usually of the same material.

Figure 12:
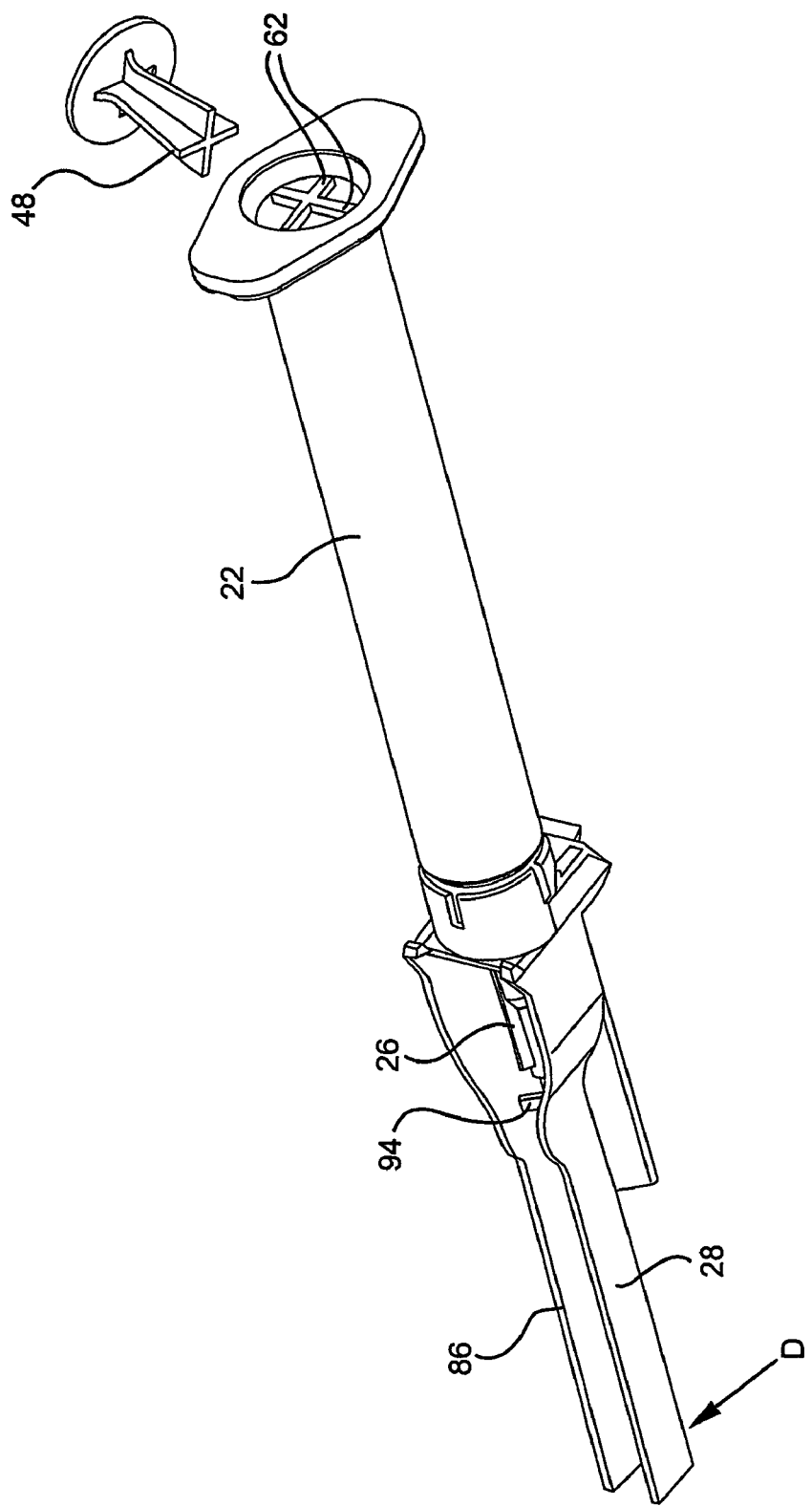
FIG. 12 is a perspective view of the syringe assembly according to the present invention, after the proximal portion of the plunger has been broken off.

After locking ring 58 is locked within the barrel via annular locking projection 45, the plunger can no longer be withdrawn from the barrel. Any attempt to withdraw the plunger from the barrel will result in the proximal portion of the plunger breaking off. Application of an axial force to the plunger in the proximal direction will cause the proximal portion of the plunger to break off at breaking points 62, since the plunger is locked within the barrel, as shown in FIG. 12.

The chamfer on locking ring 58 provides the locking ring with a one directional stiffness feature. The chamfer provides more flexibility to the plunger locking ring while the plunger is axially advanced within the barrel 22, but less flexibility of the locking ring while the plunger is axially withdrawn from the barrel. Slots 60 located on the distal side of locking ring 58 assist in achieving the one directional flexibility of the locking ring by acting as a flex point during axial advancement into the barrel. Since the slots have a minimal gap, the slots 60 only allow a minimal deflection when the plunger is being withdrawn from the barrel. In addition, the same one directional stiffness may be achieved through the presence of two thinner annular rings in place of the singe locking ring 58 and slots 60.

As discussed, the contractible portion has enough stiffness to resist premature collapse during injection, but provide enough compliance of the plunger rod during activation to achieve the axial movement required to reach the final locked position. Of course, the axial force required for an injection varies based on the gauge and size of the needle and viscosity of fluid being injected.

Figure 13:
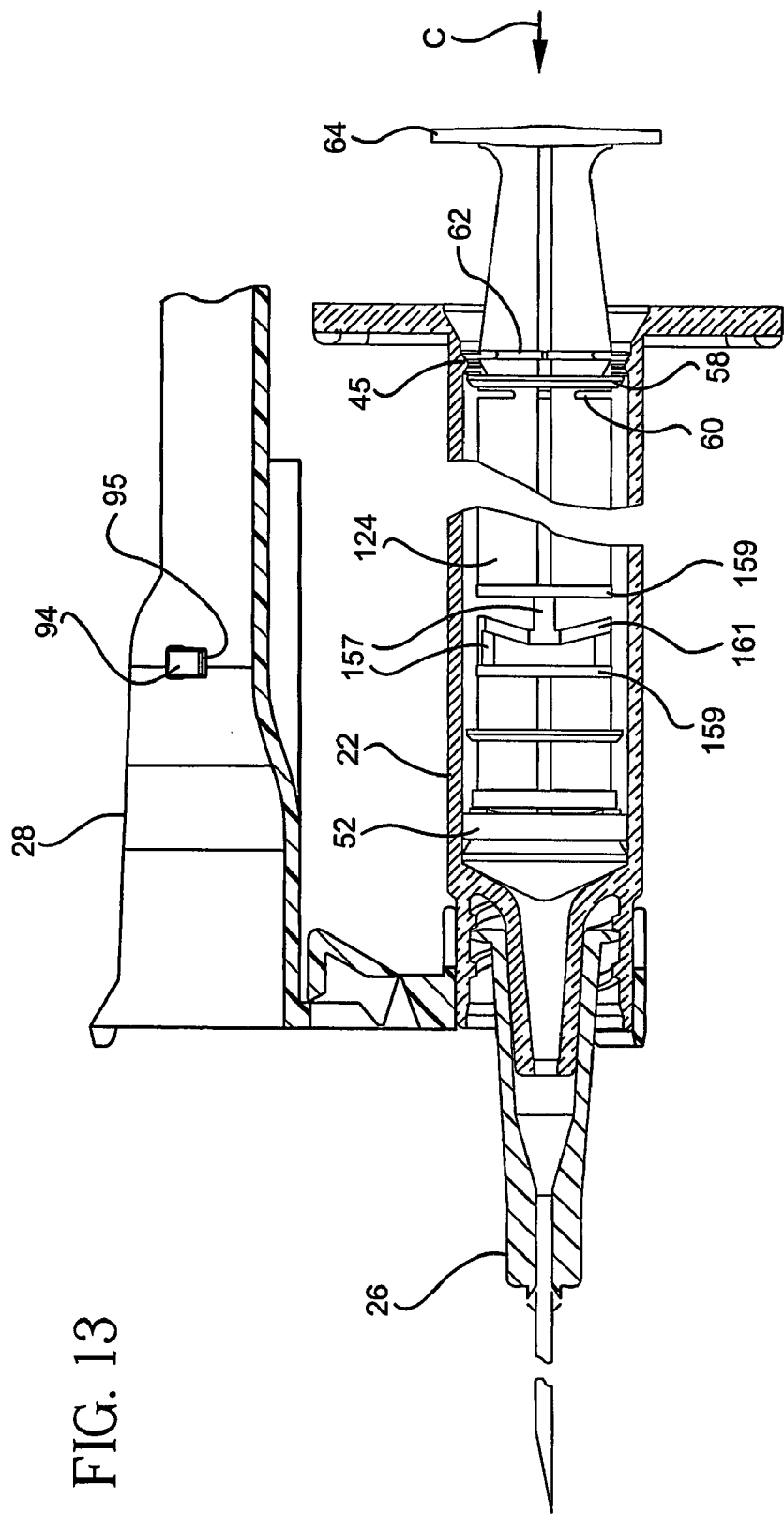
FIG. 13 is a partial cross sectional side elevation view of the syringe assembly of FIG. 6, after the plunger locking mechanism has been activated.

FIG. 13 shows the plunger of the other embodiment of the invention illustrated in FIG. 6, 6A and 6B in the locked configuration. In this embodiment, application of an additional axial force C to the proximal end of the plunger causes flexing platform 161 to flex allowing for distal axial movement of locking ring 58 into barrel 22 of the syringe. Locking ring 58 is locked in position via locking projection 45 on the barrel 22. Thus, plunger 124 is locked into the barrel and the syringe is rendered disabled and unusable. After the plunger is locked, application of an axial force in the proximal direction will cause the proximal end of the plunger to break away, completely disabling the syringe, as shown in FIG. 12.

According to the embodiment of the invention shown in FIG. 8, the additional force applied to the proximal end of the plunger will result in the flexing cross members 257 compressing together so that platforms 259 move toward each other to allow for axial movement of the locking ring 58, thereby locking the plunger within the barrel and rendering the syringe unusable.

After the syringe has been disabled, the safety shield 26 may be activated to shield the needle cannula and protect against accidental needle sticks. The safety shield is activated by application a force in the direction of arrow D in FIG. 12 to the proximal portion 88 of the shield. This will activate the living hinge, causing the shield member 86 to rotate to the position shown in FIGS. 11 and 13. Needle cannula 11 of the needle assembly is received between retaining members 94, and locking members 92 cooperate with the edge 83 to lock the shield in position.

One advantage of the present invention is the disabling features and safety shield may be activated with a single hand, further protecting the user.

The present invention contemplates the use of several safety features, either alone or in combination. The safety features include a flexing plunger with a locking ring to lock the plunger within the barrel, a compressible stopper with a locking ring to lock the plunger within the barrel, a plunger having a proximal portion which breaks off, and a needle safety shield.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A single use syringe assembly comprising:
   a barrel including a cylindrical side wall having an inside surface defining a chamber for retaining fluid and a discontinuity, an open proximal end and a distal end including a distal wall with an elongate tip extending distally therefrom having a passageway therethrough in fluid communication with said chamber;
   a needle cannula having a proximal end, a distal end and a lumen therethrough, said proximal end of said cannula being connected to said elongate tip so that said lumen is in fluid communication with said passageway;
   an elongate needle shield hingedly connected to said barrel, said needle shield having two side walls defining a longitudinal opening and a back wall between said side walls defining a recess having an interior surface, said needle shield capable of pivoting from an open position wherein said needle cannula is exposed, to a closed needle protecting position wherein said distal end of said needle cannula is within said longitudinal opening of said shield; and
   a plunger including an elongate body portion having a proximal portion, a distal portion, a contractible portion, a discontinuity, and a stopper slidably positioned in fluid-tight engagement with said inside surface of said barrel for drawing fluid into and driving fluid out of said chamber by movement of said stopper relative to said barrel, said elongate body portion extending outwardly from said open proximal end of said barrel;
   wherein when an additional distally directed force is applied to said plunger after fluid has been delivered from said chamber, said plunger shortens at said contractible portion so that said plunger discontinuity moves distally to engage said barrel discontinuity to lock said plunger in said barrel; and
   wherein said plunger further comprises at least one break point for allowing said plunger to break upon application of excessive force intended to move said plunger proximally after said plunger has been locked to said barrel.

2. The syringe assembly of claim 1 wherein said contractible portion of said plunger comprises one or more flexible elements traversing a gap in said elongate body portion, said one or more elements capable of withstanding the forces of fluid delivery and deflectable upon application of said additional force.

3. The syringe assembly of claim 2 wherein said contractible portion on said plunger further includes a cavity formed by a distal end of said plunger and an interior surface of said stopper, said plunger moving into said cavity upon application of said additional force.

4. The syringe assembly of claim 1 wherein said discontinuity on said barrel includes an inwardly directed projection on said inside surface of said barrel.

5. The syringe assembly of claim 4 wherein said inwardly directed projection is an annular ring.

6. The syringe assembly of claim 1 wherein said discontinuity on said plunger is an outwardly directed projection.

7. syringe assembly of claim 6 wherein said outwardly directed projection is an annular ring.

8. The syringe assembly of claim 1 further comprising an arm projecting from said interior surface of said needle shield, said arm having a free end positioned so that when said needle shield is pivoted to said closed position, said needle cannula moves past said free end and is trapped in said needle shield by said arm.

9. The syringe assembly of claim 1 wherein said needle shield further comprises locking members on a proximal end of said needle shield and a cooperating ledge at said distal end of said barrel so that when said needle shield is pivoted to said closed position, said locking members engage said cooperating ledge.

10. The syringe assembly of claim 1 further comprising an area of reduced cross-sectional thickness in said proximal portion of said elongate body portion of said plunger.

11. The syringe assembly of claim 1 further comprising a needle assembly including said cannula and a hub having an open proximal end containing a cavity and a distal end attached to said proximal end of said cannula so that said lumen is in fluid communication with said cavity, said needle assembly being removably attached to said tip of said barrel through engagement of said tip to said cavity so that said lumen is in fluid communication with said chamber.

12. The syringe assembly of claim 1 wherein said stopper is made of material selected form the list consisting of thermoplastic elastomers, natural rubber, synthetic rubber, thermoplastic materials and combinations thereof.

13. A single use syringe assembly comprising:
   a barrel including a cylindrical sidewall having an inside surface defining a chamber for retaining fluid, a discontinuity, an open proximal end and a distal end including a distal wall with an elongate tip extending distally therefrom having a passageway therethrough in fluid communication with said chamber;
   a needle cannula having a proximal end, a distal end and a lumen therethrough, said proximal end of said cannula being connected to said elongate tip so that said lumen is in fluid communication with said passageway;
   an elongate needle shield hingedly connected to said barrel, said needle shield having two sidewalls defining a longitudinal opening and a back wall between said side walls defining a recess having an interior surface, said needle shield capable of pivoting from an open position wherein said needle cannula is exposed, to a closed needle protecting position wherein said distal end of said needle cannula is within said longitudinal opening of said shield; and
   a plunger including an elongate body portion having a proximal portion, a distal portion, a contractible portion, a discontinuity, and a stopper slidably positioned in fluid-tight engagement with said inside surface of said barrel for drawing fluid into and driving fluid out of said chamber by movement of said stopper relative to said barrel, said elongate body portion extending outwardly from said open proximal end of said barrel;
   wherein, when applying an additional distally directed force to said plunger after fluid has been delivered from said chamber, said contractible portion shortens so that said plunger discontinuity moves distally to engage said barrel discontinuity to lock said plunger in said barrel; and
   wherein said plunger further comprises at least one break point for allowing said plunger to break upon application of excessive force intended to move said plunger proximally after said plunger has been locked to said barrel.

14. The syringe assembly of claim 13 further including means for locking said needle shield in said closed needle protecting position when said needle shield is pivoted into said closed position.

15. The syringe assembly of claim 14 wherein said locking means includes an arm projecting from said interior surface of said needle shield, said arm having a free end positioned so that when said needle shield is pivoted to said closed position, said needle cannula moves past said free end and is trapped in said needle shield by said arm.

16. The syringe assembly of claim 14 wherein said locking means includes locking members on a proximal end of said needle shield engaging cooperating ledge at said distal end of said barrel when said needle shield is pivoted to said closed position.

17. The syringe assembly of claim 13 wherein said contractible portion of said plunger comprises one or more flexible elements traversing a gap in said elongate body portion, said one or more elements capable of withstanding the forces of fluid delivery and deflectable upon application of said additional force.

18. The syringe assembly of claim 13 wherein said contractible portion on said plunger includes a cavity formed by a distal end of said plunger and an interior surface of said stopper, said plunger moving into said cavity upon application of said additional force.

19. The syringe assembly of claim 13 further comprising a needle assembly including said cannula and a hub having an open proximal end containing a cavity and a distal end attached to said proximal end of said cannula so that said lumen is in fluid communication with said cavity, said needle assembly being removably attached to said tip of said barrel through engagement of said tip to said cavity so that said lumen is in fluid communication with said chamber.

20. A single use syringe assembly comprising:
a barrel including a cylindrical sidewall having an inside surface defining a chamber for retaining fluid, a discontinuity, an open proximal end and a distal end including a distal wall with an elongate tip extending distally therefrom having a passageway therethrough in fluid communication with said chamber;
a needle assembly including a needle cannula having a proximal end, a distal end and a lumen therethrough and a hub, said hub having an open proximal end containing a cavity and a distal end attached to said proximal end of said cannula so that said lumen is in fluid communication with said cavity, said needle assembly being removably attached to said tip of said barrel through engagement of said tip to said cavity so that said lumen is in fluid communication with said chamber;
an elongate needle shield hingedly connected to said barrel, said needle shield having two sidewalls defining a longitudinal opening and a back wall between said sidewalls defining a recess having an interior surface, aid needle shield capable of pivoting from an open position wherein said needle cannula is exposed, to a closed needle protecting position wherein said distal end of said needle cannula is within said longitudinal opening of said shield; and
a plunger including an elongate body portion having a proximal portion, a distal portion, a contractible portion, a discontinuity, and a stopper slidably positioned in fluid-tight engagement with said inside surface of said barrel for drawing fluid into and driving fluid out of said chamber by movement of said stopper relative to said barrel, said elongate body portion extending outwardly from said open proximal end of said barrel;
wherein when applying an additional distally directed force to said plunger after fluid has been delivered from said chamber, said plunger shortens said contractible portion so that said plunger discontinuity moves distally to engage said barrel discontinuity to lock said plunger in said barrel, said contractible portion of said plunger comprising one or more flexible elements traversing a gap in said elongate body portion, said one or more elements capable of withstanding the forces of fluid delivery and deflectable upon application of said additional force; and
wherein said plunger further comprises at least one break point for allowing said plunger to break upon application of excessive force intended to move said plunger proximally after said plunger has been locked to said barrel.

* * * * *